US005498631A

United States Patent [19]
Gorbach et al.

[11] Patent Number: 5,498,631
[45] Date of Patent: Mar. 12, 1996

[54] METHOD FOR TREATMENT OF MENOPAUSAL AND PREMENSTRUAL SYMPTOMS

[75] Inventors: Sherwood L. Gorbach, Chestnut Hill; Barry R. Goldin, West Newton, both of Mass.; Herman Aldercreutz, Helsinki, Finland

[73] Assignee: Tufts University School of Medicine, Boston, Mass.

[21] Appl. No.: 283,678

[22] Filed: Aug. 1, 1994

Related U.S. Application Data

[63] Continuation of Ser. No. 49,006, Apr. 16, 1993, abandoned.
[51] Int. Cl.$^6$ .................................................. A61K 31/35
[52] U.S. Cl. .................................. 514/456; 514/899
[58] Field of Search ...................................... 514/456, 899

[56] References Cited

U.S. PATENT DOCUMENTS 3,864,362  2/1975  Feuer et al. ........................... 260/345.2

FOREIGN PATENT DOCUMENTS

WO93/23069  11/1993  WIPO.

OTHER PUBLICATIONS

Setchell et al., "Mammalian Lignans and Phyto–oestrogens Recent Studies on their Formation, Metabolism and Biological Role in Health and Disease," *Role of the Gut Flora in Toxicity and Cancer*, pp. 315–345 (1988).

Goldin et al., "The relationship between estrogen levels and diets of Caucasian American and Oriental immigrant women$^{1-3}$," *Am. J. Clin. Nutr.*, 1986:44:945–53 (1986).

Adlercreutz, "Urinary excretion of lignans and isoflavonoid phytoestrogens in Japanese men and women consuming a traditional Japanese diet$^{1-4}$," *Am. J. Clin. Nutr.*, 1991:54:1093–1100 (1991).

Adlercreutz et al., "Determination of Urinary Lignans and Phytoestrogen Metabolites, Potential Antiestrogens and Anticarcinogens, in Urine of Women on Various Habitual Diets," *J. Steroid Biochem.*, 1986:25:791–797 (1986).

Adlercreutz et al., "Isotope dilution gas chromatographic–mass spectrometric method for the determination of lignans and isoflavoniods in human urine, including ... ," *Clinica Chimica Acta*, 199 (1991) 263–278.

Fotsis et al., "The Multicomponent Analysis of Estrogens in Urine by Ion Exchange Chromatography and GC–MS–I. Quantitation of Estrogens After Initial . . . ," *J. Steroid Biochem.*, 1987:28:203–213 (1987).

"Dietary phyto–oestrogens and the menopause in Japan," *The Lancet*, 1992:339:1233 (1992).

*Primary Examiner*—Kimberly Jordan
*Attorney, Agent, or Firm*—Fish & Richardson

[57] ABSTRACT

A method is provided for preventing or treating symptoms of menopause, premenstrual syndrome, or a condition resulting from reduced levels of endogenous estrogen, by administering to the woman an effective amount of an isoflavonoid. The invention also features a therapeutic dietary product, containing isoflavonoids, for preventing or treating symptoms of conditions resulting from reduced or altered levels of endogenous estrogen.

12 Claims, No Drawings

METHOD FOR TREATMENT OF MENOPAUSAL AND PREMENSTRUAL SYMPTOMS

This is a continuation of application Ser. No. 08/049,006, filed Apr. 16, 1993, now abandoned.

BACKGROUND OF THE INVENTION

The present invention relates to therapies for the prevention and treatment of menopausal and premenstrual symptoms.

It has long been recognized that the sharp reduction in endogenous estrogen levels which occurs prior to menopause causes a variety of unpleasant symptoms, e.g., hot flashes, nausea, nervousness, and malaise. Currently, the symptoms of menopause are treated by estrogen replacement therapy, which has recently been shown to increase the risk of certain types of cancer, such as endometrial cancer and breast cancer. Changes in levels of endogenous estrogen may also be responsible for "premenstrual syndrome" a condition occuring in younger women prior to menstruation. Premenstrual symptoms are treated with a variety of hormonal and nonhormonal therapies, which may cause side effects. Safer and more effective therapies for both conditions continue to be sought.

SUMMARY OF THE INVENTION

The inventors have found that isoflavonoids, which are constituents of soy beans and other plants, effectively reduce the symptoms of conditions which are caused by reduced or altered levels of endogenous estrogen, e.g., menopause, and premenstrual syndrome. Without being bound by any theory, it is believed that the isoflavonoids bind to estrogen receptors, and thus exert an estrogenic response. These compounds, which are present naturally in soy-based and other plant-based foods, are safe and cause no significant side-effects. Isoflavonoids which may be administered according to the invention include genistein, daidzein, Biochanin A, formononetin, O-desmethylangolensin, and equol; these may be administered alone or in combination.

Accordingly, in one aspect, the invention features a method of preventing or treating the symptoms of menopause, premenstrual syndrome, or a condition resulting from reduced levels of endogenous estrogen, by administering to the woman an effective amount of at least one isoflavonoid. The isoflavonoid may be administered in any suitable form, e.g., in the form of a plant extract rich in isoflavonoids or in the form of a purified or synthesized isoflavonoid.

In another aspect, the invention features a therapeutic dietary product for preventing or treating symptoms resulting from reduced or altered levels of endogenous estrogen. The dietary product preferably includes a soy extract containing enriched isoflavonoids, provided in a palatable food carrier, e.g., a confectionary bar, biscuit, cereal or beverage.

Other features and advantages of the invention will be apparent from the Description of the Preferred Embodiments thereof, and from the claims.

DESCRIPTION OF THE PREFERRED EMBODIMENTS

Isoflavonoids are naturally occurring substances, found primarily in soy beans. These compounds are also found in lower concentrations in many other plants. Isoflavonoids can thus be administered to a patient by placing the patient on a diet containing high levels of soy-based food products, e.g., tofu, miso, soybeans, aburage, atuage and koridofu, or other plant products rich in isoflavonoids.

These products may not be readily available in all geographic regions (most of these foods are served predominantly in Japan), and are not be palatable to many women, particularly those accustomed to Western-style food.

Accordingly, an isoflavonoid-containing fraction can be extracted from a soy or plant product. It is preferred that the isoflavonoids be extracted and concentrated from soy bean or soy powder. Isoflavonoids are also available commercially in substantially pure form. The concentrated isoflavonoid is preferably included in a food carrier to form a dietary product. Any type of palatable carrier may be used, but, as the isoflavonoid concentrate has a strong flavor, it is preferred that the carrier include suitable flavorings to impart a different, more palatable flavor. The dietary product may be any type of food product, e.g., a confectionary bar, biscuit, cereal or beverage.

It is preferred that the dietary product contain at least 30 mg/serving total isoflavonoids. The isoflavonoid concentrate included in the dietary product preferably includes a blend primarily comprised of genistein and daidzein. The concentrate typically also contains lower levels of other isoflavonoids. Most preferably, the dietary product contains from about 10 to 30 mg/serving, more preferably about 20 mg/serving of genistein, and from about 5 to 10 mg/serving, more preferably about 7 mg/serving of daidzein. Preferably, a dietary product containing the preferred dosage of isoflavonoids would be consumed at least once per day, preferably 1 to 2 times per day depending upon the severity of the woman's symptoms.

While it is preferred that the isoflavonoid be administered in the form of a dietary product, if desired the isoflavonoid could be administered, preferably in similar dosages, in medicament form, e.g., mixed with a pharmaceutically acceptable carrier to form a tablet, powder or syrup.

EXAMPLE

The connection between diet and estrogen excretion was studied in Japanese women and men, and in a few children. The women's mean age was 50.4 (SD 18.0) years and they were all from a small village south of Kyoto and consumed a traditional Japanese low-fat diet. Isoflavonoid excretion in the urine was measured in a group of three men, three women, and three children living in Kyoto and consuming the traditional diet. We found a very high excretion of isoflavonoids in the urine of these subjects. The mean values were almost identical in the two groups and especially high excretion was found for genistein (maximum 15.5 umol per 24h in a man) and two other isoflavonoids, daidzein and equol (Table 1). All these compounds bind to estrogen receptors and have weak estrogenic activity. The excretion of the isoflavonoids in urine of the Japanese women was much higher than previously determined levels in American and Finnish women (Table 1). Excretion was high in children as in middle-aged and old people. These compounds were excreted in 100-fold to 1000-fold higher amounts than the levels of endogenous estrogens excreted by normal omnivorous women consuming a western or oriental diet (Table 1).

The excretion of the isoflavonoids in urine was associated with intake of soy products such as tofu, miso, aburage, atuage, koridofu, soybeans, and boiled beans.

It is known that Japanese women have a lower incidence of menopausal symptoms and premenstrual symptoms than the American and Finnish women.

Other embodiments are within the claims.

TABLE 1

| Urinary isoflavonoid or estrogen (nmol/day) | Japanese/ Oriental | American | Finnish |
|---|---|---|---|
| Genistein | 3440(n = 3) | . . . | 32.1(n = 12) |
| Daidzein | 2600(n = 10) | 216(n = 21) | 40.5(n = 12) |
| Equol | 2600(n = 10) | 62.8(n = 21) | 44.2(n = 12) |
| Oestrone (postmenstrual) | 4.48(n = 9) | . . . | 4.48(n = 10) |
| Oestradiol (postmenstrual) | 0.76(n = 9) | . . . | 0.94(n = 10) |
| Oestriol (postmenstrual) | 4.48(n = 9) | . . . | 4.44(n = 10) |

We claim:

1. A method of treating a medical condition in a woman caused by reduced or altered levels of endogenous estrogen, said method comprising administering to the woman an effective amount of an isoflavonoid selected from the group consisting of genistein, daidzein, Biochanin A, formononetin, o-desmethylangolensin and equol, wherein administration of the isoflavonoid increases excretion of phyto-estrogens.

2. The method of claim 1 wherein said isoflavonoid is administered in a dosage of at least 30 mg.

3. The method of claim 2 wherein said isoflavonoid is administered in said dosage at least once per day.

4. The method of claim 1 wherein genistein and daidzein isoflavonoids are coadministered.

5. The method of claim 4 wherein said isoflavonoid comprises from about 10 to 30 mg genistein and from about 5 to 10 mg daidzein.

6. The method of claim 1 wherein said isoflavonoid is administered in the form of a dietary product.

7. The method of claim 6 wherein said dietary product contains at least 30 mg/serving of said isoflavonoid.

8. The method of claim 6 wherein said dietary product is a confectionery bar containing said isoflavonoid.

9. The method of claim 6 wherein said dietary product is a cereal containing said isoflavonoid.

10. The method of claim 6 wherein said dietary product is a biscuit containing said isoflavonoid.

11. The method of claim 6 wherein said dietary product is a beverage containing said isoflavonoid.

12. The method of claim 6 wherein said dietary product is consumed by said woman at least once per day.

* * * * *

Adverse Decision In Interference

Patent No. 5,498,631, Sherwood L. Gorbach, Barry R. Goldin, Herman Adlercreutz, METHOD FOR TREATMENT OF MENOPAUSAL AND PREMENSTRUAL SYMPTOMS, Interference No. 104,576, final judgment adverse to the patentees rendered November 1, 2001, as to claims 1-12.

*(Official Gazette December 4, 2001)*

REEXAMINATION CERTIFICATE (3453rd)

United States Patent [19]

Gorbach et al.

[11] B1 5,498,631

[45] Certificate Issued Mar. 3, 1998

[54] METHOD FOR TREATMENT OF MENOPAUSAL AND PREMENSTRUAL SYMPTOMS

[75] Inventors: Sherwood L. Gorbach, Chestnut Hill; Barry R. Goldin, West Newton, both of Mass.; Herman Aldercreutz, Helsinki, Finland

[73] Assignee: Tufts University School of Medicine, Boston, Mass.

Reexamination Request:
No. 90/004,611, Apr. 23, 1997

Reexamination Certificate for:
Patent No.: 5,498,631
Issued: Mar. 12, 1996
Appl. No.: 283,678
Filed: Aug. 1, 1994

Related U.S. Application Data

[63] Continuation of Ser. No. 49,006, Apr. 16, 1993, abandoned.

[51] Int. Cl.⁶ .................................................. A61K 31/35

[52] U.S. Cl. ............................................ 514/456; 514/899
[58] Field of Search ............................ 514/456, 899

[56] References Cited

FOREIGN PATENT DOCUMENTS

| | | |
|---|---|---|
| 0129667 | 1/1985 | European Pat. Off. . |
| 0135172 | 3/1985 | European Pat. Off. . |

OTHER PUBLICATIONS

Wilcox et al., Br.Med.J., Oestrogenic Effects of Plant Foods in Postmenopausal Women, vol. 301, (1990), pp. 905–906.

*Primary Examiner*—Kimberly R. Jordan

[57] ABSTRACT

A method is provided for preventing or treating symptoms of menopause, premenstrual syndrome, or a condition resulting from reduced levels of endogenous estrogen, by administering to the woman an effective amount of an isoflavonoid. The invention also features a therapeutic dietary product, containing isoflavonoids, for preventing or treating symptoms of conditions resulting from reduced or altered levels of endogenous estrogen.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2–12, dependent on an amended claim, are determined to be patentable.

1. A method of treating [a medical condition in a woman caused by reduced or altered levels of endogenous estrogen] *symptoms of menopause or premenstrual syndrome in a woman*, said method comprising administering to the woman an effective amount of [an] *a naturally occurring, isolated* isoflavonoid *which exhibits estrogenic activity, wherein said isoflavonoid is* selected from the group consisting of genistein, daidzein, Biochanin A, formononetin, O-desmethylangolensin, and equol, wherein administration of the isoflavonoid increases excretion of phytoestrogens.

* * * * *